United States Patent [19]

Lewis

[11] Patent Number: 5,591,586
[45] Date of Patent: Jan. 7, 1997

[54] HYBRIDIZATION MAPPING OF NUCLEIC ACIDS

[76] Inventor: Hunner C. Lewis, 2111 Ashby Ave. #11, Berkeley, Calif. 94705

[21] Appl. No.: 494,928

[22] Filed: Jun. 26, 1995

[51] Int. Cl.⁶ ............................. C12Q 1/68; C12N 15/00
[52] U.S. Cl. .................... 435/6; 935/78; 935/80
[58] Field of Search ................................ 435/6; 935/78, 935/80

[56] References Cited

U.S. PATENT DOCUMENTS 5,217,863   6/1993   Cotton et al. ............................. 435/6

OTHER PUBLICATIONS

Galas and Schmitz (1987) Nucleic Acids Research 5:3157–3170.
Berk and Sharp (1977) Cell 12:721–732.
Kornberg and Baker, *DNA Replication*, 2nd edition (1992), p. 415.
Umthun et al. (1994) Nucleic Acids Research 22:4432–4440.
Hollingsworth et al. (1994) Nucleic Acids Research 22:1138–1146.
Wang et al. (1993) J. Biol. Chem. 268:10681–5.

*Primary Examiner*—W. Gary Jones
*Assistant Examiner*—Amy Atzel

[57] ABSTRACT

A method is described which enables an investigator to locate where upon one single-stranded target nucleic acid molecule one or more separate single-stranded nucleic acid probe molecules hybridize. The method for determining where the probe hybridizes to the target is to allow the probe, present in excess relative to the target, and end-labeled (or labelable) target an opportunity to hybridize with one another after having been denatured together, if originally double-stranded, in a common reaction vessel and to then lightly digest the product of their hybridization with an agent that preferentially cleaves double- or single-stranded nucleic acids, depending upon the variation of hybridization mapping employed. The digestion should be such that, on average, each molecule which is cleaved is cleaved once. The cleaved reaction products are then fractionated by size to reveal the location of hybridization by reference to the pattern of signals produced by the label.

16 Claims, 2 Drawing Sheets

FIGURE 2
METHODS OF HYBRIDIZATION MAPPING
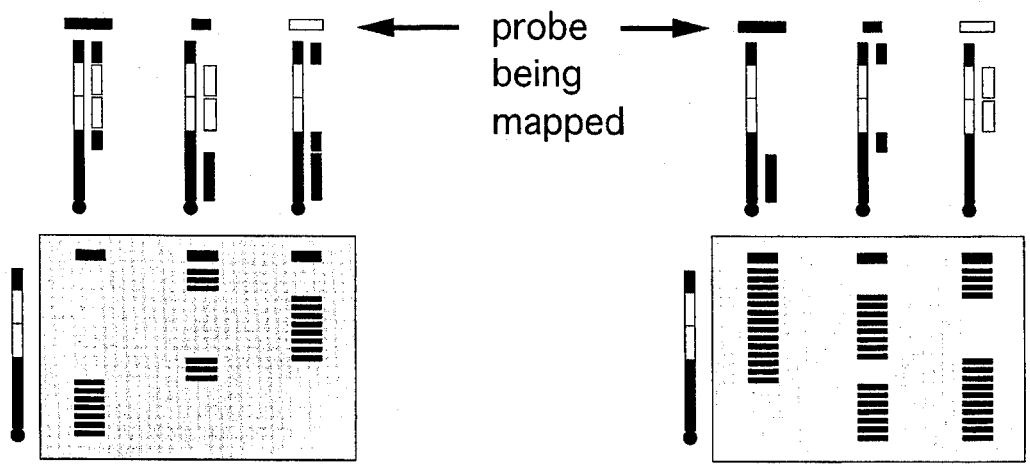
A. Positive, single-strand-cutting hybridization mapping.
B. Negative, single-strand-cutting hybridization mapping.
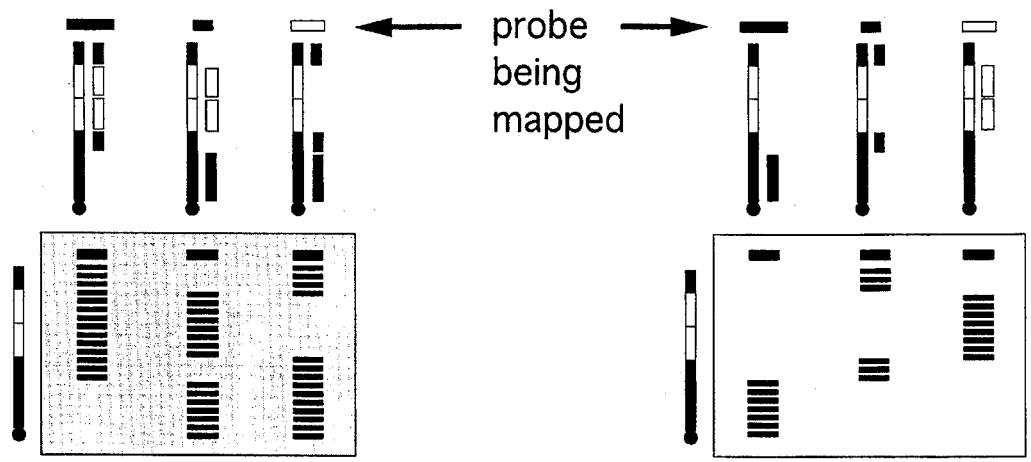
C. Negative, double-strand-cutting hybridization mapping.
D. Positive, double-strand-cutting hybridization mapping.

HYBRIDIZATION MAPPING OF NUCLEIC ACIDS

BACKGROUND OF THE INVENTION

1. Field of the Invention

The present invention is a method for mapping nucleic acid molecules. More specifically, it is a method for determining where one oligonucleotide hybridizes to another oligonucleotide.

2. Description of Related Disclosures

It is sometimes useful to determine where one oligonucleotide sequence resides within another. One familiar example of this is the preparation of a conventional restriction map, a technique reviewed by Nathans and Smith. If a circular plasmid is digested with one or more restriction enzymes which are known to cut, in combination, two or more times within the plasmid, a restriction map can sometimes be prepared to show where the restriction enzymes cut the plasmid and, equivalently, how the fragments produced by the digestion are arranged within the plasmid. Once a restriction map has been prepared it may then be said that a certain fragment resides at a certain location within the plasmid.

The conventional preparation of such a restriction map involves performing multiple restriction digests using individual enzymes and combinations of enzymes. The digestions are followed by an analysis of the lengths of the fragments produced. This analysis involves considering all of the potential permutations that the fragments might embody and becomes factorially more difficult as the number of fragments increases. In many cases an unambiguous map cannot be prepared. Restriction maps also require that more than one restriction enzyme be mapped at a time. Moreover, conventional mapping procedures cannot use the data from a single enzyme digestion to prepare a map of that enzyme.

Hybridization mapping avoids several of the problems associated with conventional restriction mapping. It does not require that multiple restriction digests be performed to create a map. Nor does it involve the ambiguity and potential failure entailed in determining the correct permutation of fragments produced by multiple digests.

Another method for locating one oligonucleotide within another is the method of Berk and Sharp for locating the portion of an mRNA transcript within a DNA clone which is suspected of having served as a transcription template for the transcript. The Berk-Sharp method involves preparing multiple restriction maps of the DNA clone by the method described above, determining the complete size of the transcripts of interest and then determining the sizes of the hybrids formed between the transcripts and the different restriction fragments from the different restriction digests. The determination of size information is done by completely digesting away the single-stranded regions of the transcript-restriction fragment hybrids with S1 nuclease and then sizing the double-stranded hybrids on an electrophoretic gel. The size information can then be analyzed to locate the transcription location on the full restriction map of the large DNA clone.

Hybridization mapping does not require that either the target or probe oligonucleotides be restriction mapped beforehand, as does the Berk-Sharp method. The Berk-Sharp method also requires that a significant amount of analysis be performed on the data produced and often requires that additional restriction maps of the DNA clone be prepared by other methods to produce an unambiguous result. Another deficiency of the Berk-Sharp method is that it is designed to only work with RNA-DNA hybrids whereas hybridization mapping will work with DNA-DNA hybrids as well as RNA-DNA hybrids.

Another situation in which it is useful to learn where one oligonucleotide resides within another is when sequencing a very long molecule such as a chromosome. One current method of long-molecule sequencing is to randomly divide the long molecule into multiple small overlapping fragments, sequence the fragments, and then use a computer to determine the regions of overlap. This "shotgun" sequencing technique results in the long molecule being sequenced multiple times and there are often problems in obtaining the last few fragments needed to produce a complete sequence of the molecule.

REFERENCES

Berk, A. J. and P. A. Sharp. 1977. Sizing and mapping of early adenovirus mRNAs by gel electrophoresis of S1 endonuclease-digested hybrids. Cell 12,721.

Church, G. M. and S. Kieffer-Higgins. 1988. Multiplex DNA sequencing. Science 240,185.

Galas, D. J. and A. Schmitz. 1978. DNAase footprinting: a simple method for the detection of protein-DNA binding specificity. Nucleic Acids Research 5,3157.

Nathans, D. and H. O. Smith. 1975. Restriction endonucleases in the analysis and restructuring of DNA molecules. Annual Review of Biochemistry 44,273.

Perbal, B. *A Practical Guide to Molecular Cloning.* 2nd ed. 1988.

Sambrook, J., Fritsch, E. F. and T. Maniatis. *Molecular Cloning.* 2nd ed. 1989.

BRIEF DESCRIPTION OF THE INVENTION

The present invention provides a method for showing where one or more fragments of nucleic acid are complementary to another nucleic acid molecule.

Hybridization mapping, in its most basic form, is a method of visualizing the hybridization relationship of two nucleic acid molecules. It enables an investigator to locate where upon one single-stranded nucleic acid molecule, called the target, one or more single-stranded nucleic acid molecules, called probes, hybridize. The method for determining where the probe hybridizes to the target is to allow the probe and end-labeled (or labelable) target an opportunity to hybridize with one another after having been denatured together, if originally double-stranded, in a common reaction vessel and to then lightly digest the product of their hybridization with an agent that preferentially cleaves double- or single-stranded nucleic acids, depending upon the variation of hybridization mapping employed. The digestion should be such that, on average, each molecule which is cleaved is cleaved once and at random. The cleaved reaction products are then fractionated by size and visualized to reveal the location of hybridization by reference to the pattern of signals produced by the label.

When mapping a double-stranded fragment against another double-stranded fragment, it is more accurate to say that hybridization mapping shows where one strand of the probe molecule hybridizes with a complementary strand of the target molecule after both molecules have been denatured and then allowed to anneal with one another. This information will sometimes be useful in and of itself. When elaborated to map the location of multiple smaller molecules on a larger molecule, hybridization mapping provides an alternative to the construction of conventional restriction maps.

The usefulness of hybridization mapping is determined by how the target and probes are chosen. To use hybridization mapping in the construction of a restriction map, the target is defined to be the molecule being mapped and the probes are the restriction fragments produced by one or more restriction enzymes acting on the target molecule. Hybridization mapping can be used to show where an RNA transcript or its cognate cDNA hybridize within a cloned DNA molecule if the clone is used as the target and the transcript is used as the probe. Hybridization mapping may also be useful in determining the arrangement of nucleic acid sequences within a larger sequence when the subsequences are known in advance and the only question to be answered is the order of the subsequences.

BRIEF DESCRIPTION OF THE FIGURES

FIG. 2 indicates the four possible methods of hybridization mapping. Three probes are mapped against a common target.

DESCRIPTION OF THE PROCEDURE

Definitions

Figure 1:
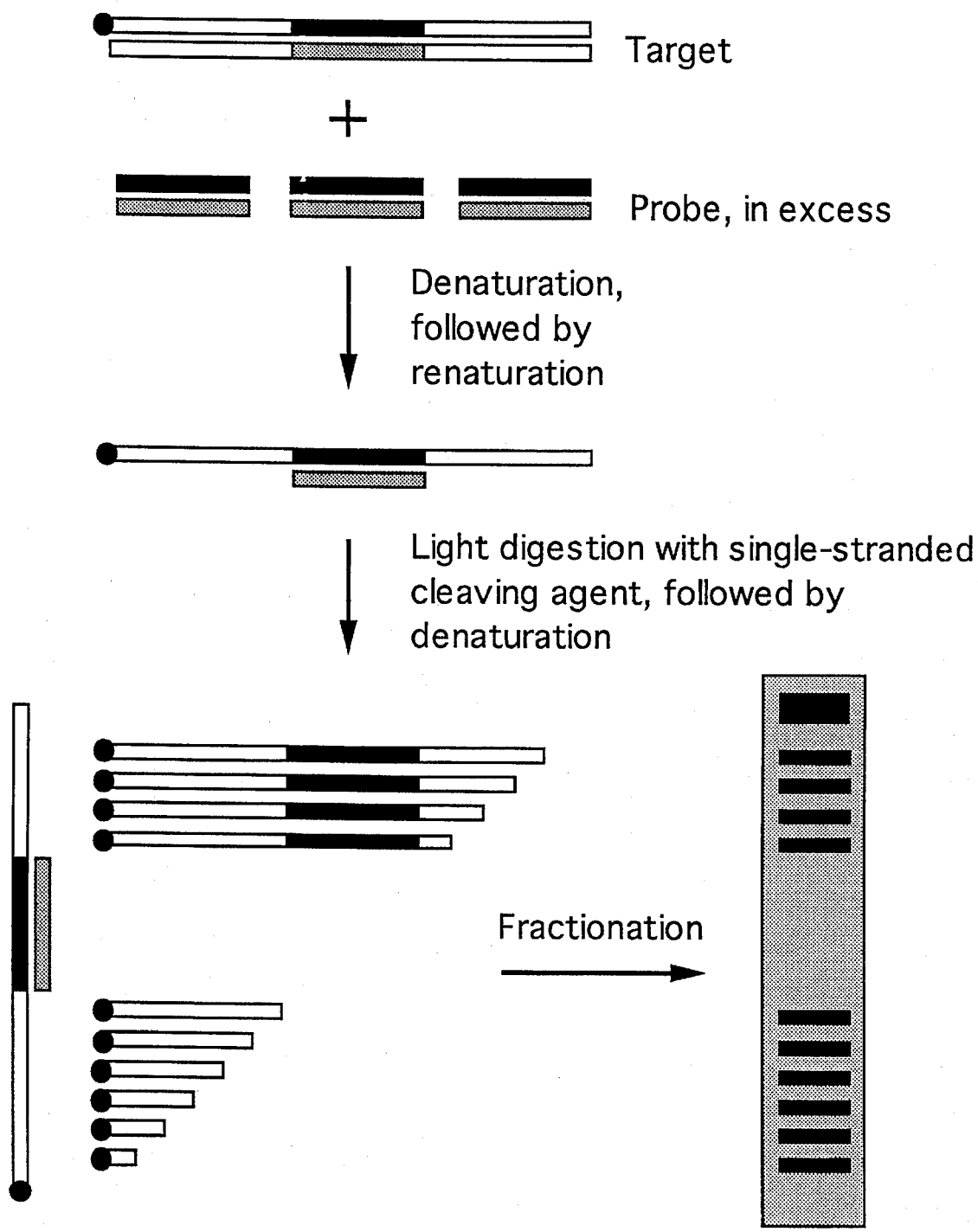
FIG. 1 shows one method of hybridization mapping. A single probe is mapped against a target.

In the following descriptions of hybridization mapping the terms "target" and "probe" are used. A target or target molecule is defined to be a nucleic acid, either RNA or DNA, which is suspected or known to contain a sequence which is substantially complementary to a sequence, or sequences, contained in a probe. The target may initially be single-stranded or multiply-stranded. If multiply-stranded, it must be denatured before hybridization with the probe. The strandedness of targets and probes will be clear from the context in which they are discussed. The target must be end-labeled at some point in the procedure. In most cases the target will be a longer molecule than the probe.

A probe or probe molecule is defined to be a nucleic acid, either RNA or DNA, which is suspected or known to contain a sequence of bases which is, at least in part, complementary to a sequence or sequences contained in a target. The probe may be singly or multiply stranded. If multiply-stranded, the probe needs to be denatured prior to hybridization with the target. In most cases a probe will be a shorter molecule than the target. The question answered by the hybridization mapping procedure is whether, and where upon the length of the target molecule, the probe molecule hybridizes.

The term "sibling strand" refers to the relationship between the two complementary components of an individual double-stranded molecule.

Materials and General Methods

Unless otherwise stated hybridization mapping uses standard nucleic acid manipulation procedures. In particular, the procedures used to collect, prepare, cut, label, denature, renature, fractionate, radiograph and/or fluorograph nucleic acids as part of the hybridization mapping reaction are the same as those used in conventional academic and industrial laboratories. These procedures are described in references such as Maniatis and Perbal. Individual hybridization and cleavage conditions (especially temperature, reactant concentrations, hybridization time and cleavage time) need to be determined experimentally and will depend upon the lengths of the probe and the target, and the concentrations of the probe, target and cleavage agent.

Detailed Description of the Procedure

The method for determining where one strand of the probe hybridizes to a particular strand of the target is to first allow the probe and end-labeled (or labelable) target an opportunity to hybridize with one another after each has been made single-stranded. The probe must be present at a higher concentration than the target. In most cases single-strandedness will be achieved by combining the target and probe(s) together in a common reaction vessel and then raising the reaction temperature above the melting point of both types of molecules. In other cases the target and/or the probes may be brought to the hybridization reaction already single-stranded.

After preparing the target and probe(s) so that they are single-stranded, they are then permitted to partially rehybridize with one another. In most cases the rehybridization will be effected by lowering the reaction temperature to a value below the melting temperature of the hybridization products. Because the probe is at a higher concentration than the target the predominant rehybridization reactions will be probe hybridizing to probe and probe hybridizing to target. Reaction conditions such as target concentration and rehybridzation time must be determined experimentally to avoid target-to-target rehybridization, which will interfere with subsequent cleavage. Probe rehybridizing to probe is an inconsequential side reaction.

The products of the rehybridization reaction are then lightly digested with an agent that preferentially cleaves double- or single-stranded nucleic acids, depending upon the variation of hybridization mapping employed. The term "cleave" is meant to denote the rupturing of one or more adjacent covalent bonds in the nucleic acid molecule in such a way as to result in the subsequent separation of the two oligonucleotides which flank the ruptured bond or bonds. The terms "cleave" and "cut" are used interchangeably.

The nature of the cleaving agent should be such that it cleaves its target randomly or pseudorandomly. "Randomly" is a relative term. For example, a 4-cutter restriction enzyme would not be considered to cut randomly in a 2 kbp plasmid, but might be an effective random cutter for a 1,000 kbp YAC being mapped by probes larger than 100 kbp. This is because a 4-cutter restriction enzyme will, on average, cut once every 256 bp, which is often enough in a 100 kbp region to produce a signal for hybridization mapping. The 4-cutter would be cutting pseudorandomly in such a case. The term "random" is meant to indicate that the cleavage agent has no higher affinity for one location or sequence on the target than any other. Such cleaving agents include single-stranded-specific endonucleases, double-stranded-specific endonucleases, and chemical cleaving agents which preferentially cleave single- or double-stranded molecules. Specific cleaving agents which cleave single-stranded oligonucleotides in a random or pseudorandom way include S1 Nuclease, Mung Bean Nuclease, and potassium permanganate. Cleaving agents which cleave double-stranded oligonucleotides in a random or pseudorandom way include DNase I. The optimal concentration of cleaving agent should be such that, on average, each hybrid molecule that is cleaved is only cleaved once. The concentration and cutting time of the cleaving agent must be determined experimentally for each hybridization procedure.

The cleaved rehybridization reaction products are then denatured and fractionated by size and the label is visualized to reveal the location of hybridization. A preferred embodiment for fractionating is a denaturing electrophoretic gel. There will be a variety of reaction byproducts running down such a gel. The only products of interest are those single-stranded, end-labeled (or labelable) target fragments produced by the cleavage agent.

Visualization may be accomplished by an autoradiograph of the gel. An alternative method of visualization is to prepare a Southern blot of the gel and then probe the blot with a short oligonucleotide attached to a colorigen or fluorogen. This alternative method is a technique for labeling the target after the hybridization reaction.

End-labeling of the target can occur before hybridization with probe(s) or after fractionation and can be performed in several ways depending upon what is known about the target's end or flanking sequences. An end-labeling method such as $^{32}$P-labeling described for Maxam-Gilbert sequencing and protein footprinting in the Sambrook reference can be used before hybridization in cases where the target or its vector is sufficiently characterized so as to know that restriction enzymes used to produce asymmetrically labeled molecules do not cleave the target at interior locations. In other cases, where the conventional labeling procedure interferes with the restriction-mapping cleavages, the post-fractionation hybridization-labeling technique employed by Church for multiplex sequencing will be more appropriate. Church's method involves hybridizing the fractionated and Southern blotted products with a labeled oligonucleotide that is complementary to one end of the target. If Church's method is used, it may be useful to include or exclude (depending on the variant of hybridization mapping) an unlabeled version of the labeling oligonucleotide to protect the target's labelable region from cleavage. In many cases the target to be mapped will be a DNA molecule that has been cloned into a well-characterized (if not completely sequenced) vector such as a plasmid, cosmid, phage, phagemid or YAC. This means that the sequences which flank the target will be known and this information will be useful in determining how the target can be end-labeled.

When the pattern of fractionated reaction products are examined the investigator will be able to detect where the probe hybridized to the target by observing the presence or absence (depending on the hybridization mapping method) of labeled bands or smears of label. It may be helpful to run a "ladder" of randomly sheared or cut target on the same gel as the mapping reactions to provide a reference for the individual reactions.

FOUR METHODS OF HYBRIDIZATION MAPPING

Hybridization mapping can be performed with single-strand-specific cleavage agents or double-strand-specific cleavage agents. For each of these two alternate methods there are two sub-variant methods which determine how the location of the mapped probe will be indicated after fractionation. These two variants and their sub-variants are described below.

METHOD 1

Positive Single Strand Cutting (PSSC)
Hybridization Mapping

This description of hybridization mapping refers to lane 1 of FIG. 2a. The probe being mapped is referred to as "B" and is shown in the figure as gray. Probes "A" and "C" are black and white, respectively.

The end-labeled (or labelable) target is combined with double-stranded probes "A" and "C" present in substantial excess (to help forestall competitive re-annealing of the target with itself) in a reaction tube. The concentration of target needs to be adjusted by dilution to disfavor the rehybridization of sibling target strands. This dilution can be of absolute or relative target sequence concentration. The reaction is accomplished by denaturing the target and probes and then allowing them to re-anneal with one another. For this example the DNA is heated beyond the Tm and then cooled to permit hybridization of the excess probe to the target. A single-strand-specific cutting reagent such as S1 nuclease or mung bean nuclease is then added to a concentration that permits each single-stranded region which is cut to be cut once. Strands from probes "A" and "C" will have annealed to their respective complements on the target and these regions of local hybridization, being double stranded, will not be susceptible to the single-stranded-specific cleavage agent. Since there is no "B" probe in the reaction mixture and the concentration of target is low enough to disfavor significant target rehybridization, the regions complementary to "B" will be single stranded and susceptible to cleavage. The reaction is then stopped to prevent over-digestion and the reaction mix is run on a denaturing gel that permits resolution of fragments at least as small as the smallest probe. The relative position of the "B" probe will appear on the gel as a dark smear after autoradiography. The fractionation and visualization process is amenable to continuous fractionation procedures and florescent visualization and these procedures may be preferable for some targets. A comparison of similar reactions for each unique probe will provide a complete map of the target. See all lanes of FIG. 2a.

METHOD 2

Negative Single Strand Cutting (NSSC)
Hybridization Mapping

A second method, negative single-strand-cutting hybridization mapping, involves performing the same procedure as above except that each mapping reaction includes only the probe to be mapped (instead of "all but the targeted probe"). This method may entail more problems than the prior method because the long tracts of the target left uncovered by complementary probe will be available to rehybridize to the sibling target strand or to form internal hybrids with itself. Either situation would interfere with a single-strand-specific cutting agent. The gels are run as described in the first method and the location of the particular probe is revealed by the absence of bands instead of their presence. See FIGS. 1 and 2b.

METHOD 3

Negative Double Strand Cutting (NDSC)
Hybridization Mapping

A third method reverses the second method in that reagents are used (i.e. DNAase I) which preferentially cut double-stranded polynucleotides. If all probes but the one to be mapped are permitted to anneal to the target and then the annealed (double-stranded) region is cut once at random and then fractionated by size, the banding pattern will be read in the same way as the negative SSC mapping described above. The probe being mapped will appear as a gap among bands or smears. This form of mapping is similar to the footprinting of Galas and Schmitz except that a probe, not a nucleic-acid-binding protein, is being located. See FIG. 2c.

METHOD 4

Positive Double Strand Cutting (PDSC) Hybridization Mapping

A fourth method is to anneal only the probe to be mapped to the target and then cut once and at random with a double-strand specific reagent. After fractionation the presence of bands will indicate the relative position of the probe being mapped. See FIG. 2d.

EXAMPLE 1

Restriction Hybridization Mapping

One method of surveying the structure of a DNA fragment is to create a restriction map. When an investigator digests a plasmid with a single restriction enzyme which cleaves the plasmid at several points, and then separates and sizes those fragments by means of an electrophoretic gel, he or she has obtained information about how many enzyme cuts are made, but no information is provided about the relative positions the different sized fragments occupy within the plasmid. To prepare a map of a plasmid or other DNA molecule one must perform multiple digests with single and multiple restriction enzymes and then analyze the pattern of fragments fractionated by size on an electrophoretic gel. As the number of fragments to be mapped increases, the difficulty of deducing the restriction map increases approximately as the factorial of the number of fragments.

Hybridization mapping may be used to determine the order of the restriction fragments produced by digestion of a nucleic acid fragment with a single restriction enzyme. The target is the fragment of DNA to be mapped. The probes are the restriction fragments produced by a particular restriction-enzyme digest of the target fragment.

Consider the hybridization mapping of the largest restriction fragment produced by the digestion of pUC18 with EcoRI and HindIII. In this example the large fragment will be hybridization mapped by the fragments resulting when this large fragment is digested with PleI. In the restriction map of pUC18 shown below the conventional base-numbering system is used. pUC18 is a circular plasmid and the zero point and 2686 point on the map below do not indicate restriction sites.

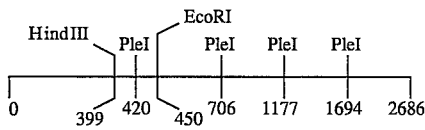

The first step is to cleave a sample of pUC18 with EcoRI, HindIII and PleI. The cleavage reaction is run on a gel and the four largest fragments (256 bp, 471 bp, 517 bp and 1391 bp) are collected by electroelution or some other method. These fragments are the probes that will be used to map the EcoRI-HindIII fragment. The other two small fragments produced in this multiple cleavage reaction will not be collected or used in further reactions because they are not part of the large EcoRI-HindIII fragment being mapped.

The second step is to prepare an end-labeled sample of the large EcoRI-HindIII fragment to be mapped. This is accomplished by cutting another sample of pUC18 with EcoRI and then running a standard kinasing reaction to label the 5' phosphate at each end of the fragment with $^{32}$P. Once labeled, the molecule is then cut with HindIII to cleave off a 51 bp fragment from one end, thereby producing the uniquely end-labeled, 2635 bp target for the hybridization mapping reaction. Note that within this small 51 bp fragment is a single PleI restriction site at position 420 which will be lost and is not relevant to any of the hybridization mapping reactions.

In this example there is no need to separate the two different-sized, end-labeled molecules. The smaller one will show up as a small, radioactive smear near the bottom of the electrophoretic gel, or it may be allowed to run off the bottom of the gel. In other cases it may be necessary to isolate the larger labeled target before proceeding to the hybridization reaction.

Once the four PleI probe fragments and the end-labeled target fragment have been prepared as described above, the hybridization mapping reaction can be run. In this example, Method 1 (PSSC hybridization mapping) will be used.

To map the location of the smallest probe, an excess of the larger three fragments is added along with an aliquot of the end-labeled target to a reaction tube containing a reaction buffer appropriate for digestion with S1 nuclease and with a target concentration sufficient to inhibit extensive rehybridization of the sibling target strands during the course of the hybridization and cutting. The probe being mapped is not added. The mixture is heated to an appropriate temperature for a sufficient time to denature the target and probe molecules. The mixture is then cooled to an appropriate temperature so that the probes can hybridize to the target. Once the target-probe hybridization reaction is complete, an appropriate amount of S1 nuclease is added for an appropriate length of time to effect the partial cutting of the target-probe hybrids and then the reaction is stopped. The concentration of S1 and the duration of the cleavage reaction will need to be optimized by prior experiments to get appropriate cutting.

Determination of the optimal target, probe and S1 nuclease concentrations, as well as S1 nuclease digestion time requires premapping experimentation. A typical premapping experiment would involve choosing an intermediate-sized probe and running a series of mapping experiments to optimize the reaction parameters and is described below.

Titration reactions should be run with varied concentrations of target DNA in S1 cutting buffer. Each of the following test reactions should be run in 10 ul, 20 ul 50 ul and 100 ul volumes in order to optimize the target concentration. Target DNA amounts should be 0.1 pmole, 0.5 pmole, 1 pmole, 5 pmole, 10 pmole, 50 pmole, 100 pmole and 1 nmole. For each of these reactions the concentration of the probe should be varied so that 10X (times) target, 20X target, 50X target and 100X target are tested. For example, 10X target means that for a target amount of 1 pmole, a probe amount of 10 pmole should be included in the reaction. Hybridization times should also be varied. One minute, 10 minutes, 20 minutes, 50 minutes, 100 minutes and 500 minutes are suitable variants.

For each of the above reactions the amount of S1 nuclease should be varied so that at least five different concentrations are tested. The amounts of S1 nuclease which should be tested are 0.01 unit, 0.1 unit, 1 unit, 5 units, 10 units, 50 units and 100 units. For each of these sub reactions at least five digestion times should be examined. These times should be 1 minute, 5 minutes, 10 minutes, 50 minutes and 100 minutes. All reactions are quenched with an S1 stop buffer. The DNA is precipitated with 70% EtOH in preparation for gel electrophoresis.

When the preceding set of titration reactions are run and visualized, an optimal set of reaction parameters can be selected and refined for the subsequent complete mapping operations.

The optimized procedure is performed for each of the remaining three probes to be mapped. For each probe to be mapped, each of the other three probes are added to a single mixture containing the target and the procedure described above is performed. The four individual reactions required to map each of the four probes can be run concurrently.

Once all of the reactions have been run, each precipitated reaction mixture is run in a separate lane on a common denaturing gel. The gel concentration should be such that fragments the size of the probes can be easily distinguished from one another. Ideally there will be a smooth spectrum of sizes ranging from molecules the size of the target near the top of the gel to single-base molecules at the bottom of the gel. On most gels this spectrum will appear as a smear of radioactivity rather than a ladder of discrete bands.

Once the gel has been run, it is developed to produce an autoradiograph. The autoradiograph is then examined to determine the relative positions of the individual probes. The relative positions are indicated by bands or smears indicating where the target molecule was cleaved by S1 nuclease.

EXAMPLE 2

Recursive Genomic Sequencing

Hybridization mapping in this second example is a demonstration of how restriction hybridization mapping can be used as one fork of a recursive procedure to facilitate the sequencing of a component (lambda clone, cosmid, YAC, etc.) of a genomic library. The other fork is conventional Sanger sequencing. In this example the component is considered to be a large one, in excess of 100 kbp. Hybridization mapping is used repetitively to order the fragments produced at each stage of the process. It is literally a divide and conquer process, whereby the larger fragment is divided into smaller fragments by one or more restriction enzymes. After digestion the resulting fragments are used to hybridization map the larger parent fragment from which they originated, the order is noted and then each of the new fragments are digested with another group of one or more restriction enzymes and the resulting fragments are used as probes to map their parents. The procedure is repeated for each generation of fragments until the fragments are small enough to be directly cloned and sequenced by the Sanger method. The information regarding fragment order produced by hybridization mapping is retained at each stage and finally used to order the Sanger-sequenced fragments produced at the last stage.

Current sequencing projects tend to be inefficient. Shotgun sequencing often requires that a given fragment of DNA be sequenced multiple times to assure a complete sequence. The method of Example 2 could theoretically reduce the number to one.

CONCLUSION

The object of this invention is to determine where upon one single-stranded nucleic acid molecule one or more separate single-stranded nucleic acid molecules hybridize. The method of the invention is analogous to the protein footprinting procedure of Galas and Schmidt, except that nucleic acid hybridization distinguishes a region of the target molecule as being complementary to another nucleic acid, instead of being a binding site for a nucleic-acid-binding protein.

Although this invention has been described with reference to specific embodiments, it is understood that modifications and variations may occur to those skilled in the art. Such other embodiments and modifications are intended to fall within the scope of the appended claims.

What is claimed is:

1. A method of determining where at least one probe nucleic acid hybridizes with an end-labeled target nucleic acid comprising the steps of:

(a) preparing the target and probe nucleic acids so that they are single-stranded;

(b) hybridizing the single-stranded target and probe nucleic acids with one another, thereby forming hybridization products;

(c) digesting the hybridization products with a cleaving agent which preferentially cleaves single-stranded nucleic acids under such conditions that each hybridized nucleic acid which is cleaved in an unhybridized region is cleaved once, on average, and at random;

(d) fractionating the digested products by size to form a pattern of fractionation products;

(e) detecting the pattern of fractionation products by detecting said end-label; and (f) determining where the probe nucleic acid hybridizes to the target by examining the pattern of labeled fractionation products.

2. The method of claim 1, wherein the target nucleic acid is DNA or RNA and the probe nucleic acid(s) is DNA or RNA.

3. A method of determining where at least one probe nucleic acid hybridizes with an end-labeled target nucleic acid comprising the steps of:

(a) preparing the target and probe nucleic acids so that they are single-stranded;

(b) hybridizing the single-stranded target and probe nucleic acids with one another, thereby forming hybridization products;

(c) digesting the hybridization products with a cleaving agent which preferentially cleaves double-stranded nucleic acids under such conditions that each hybridized nucleic acid which is cleaved in a hybridized region is cleaved once, on average, and at random;

(d) fractionating the digested products by size to form a pattern of fractionation products;

(e) detecting the pattern of fractionation products by detecting said end-label; and (f) determining where the probe nucleic acid hybridizes to the target by examining the pattern of labeled fractionation products.

4. The method of claim 3, wherein the target nucleic acid is DNA or RNA and the probe nucleic acid(s) is DNA or RNA.

5. A method for determining where at least one probe nucleic acid hybridizes with a target nucleic acid comprising the steps of:

(a) preparing the target and probe nucleic acids so that they are single-stranded;

(b) hybridizing the single-stranded target and probe nucleic acids with one another, thereby forming hybridization products;

(c) digesting the hybridization products with a cleaving agent which preferentially cleaves single-stranded nucleic acids under such conditions that each hybridized nucleic acid which is cleaved in an unhybridized region is cleaved once, on average, and at random;

(d) fractionating the digested products by size to form a pattern of fractionation products;

(e) detecting the pattern of fractionation products by hybridization-labeling with a labeled nucleic acid complementary to one end of the target nucleic acid; and (f) determining where the probe nucleic acid hybridizes to the target by examining the pattern of labeled fractionation products.

6. The method of claim 5, wherein the target nucleic acid is DNA or RNA and the probe nucleic acid(s) is DNA or RNA.

7. A method for determining where at least one probe nucleic acid hybridizes with a target nucleic acid comprising the steps of:

(a) preparing the target and probe nucleic acids so that they are single-stranded;

(b) hybridizing the single-stranded target and probe nucleic acids with one another, thereby forming hybridization products;

(c) digesting the hybridization products with a cleaving agent which preferentially cleaves double-stranded nucleic acids under such conditions that each hybridized nucleic acid which is cleaved in a hybridized region is cleaved once, on average, and at random;

(d) fractionating the digested products by size to form a pattern of fractionation products;

(e) detecting the pattern of fractionation products by hybridization-labeling with a labeled nucleic acid complementary to one end of the target nucleic acid; and (f) determining where the probe nucleic acid hybridizes to the target by examining the pattern of labeled fractionation products.

8. The method of claim 7, wherein the target nucleic acid is DNA or RNA and the probe nucleic acid(s) is DNA or RNA.

9. A method of producing a map of a target nucleic acid comprising the steps of:

(a) producing fragments of said target nucleic acid;

(b) separating, collecting and forming probes from said fragments; and (c) determining where each of said probes hybridizes to the target nucleic acid according to the method of claim 1, thereby producing a map of the target nucleic acid.

10. A method of producing a map of a target nucleic acid comprising the steps of:

(a) producing fragments of said target nucleic acid;

(b) separating, collecting and forming probes from said fragments; and (c) determining where each of said probes hybridizes to the target nucleic acid according to the method of claim 3, thereby producing a map of the target nucleic acid.

11. A method of producing a map of a target nucleic acid comprising the steps of:

(a) producing fragments of said target nucleic acid;

(b) separating, collecting and forming probes from said fragments; and (c) determining where each of said probes hybridizes to the target nucleic acid according to the method of claim 5, thereby producing a map of the target nucleic acid.

12. A method of producing a map of a target nucleic acid comprising the steps of:

(a) producing fragments of said target nucleic acid;

(b) separating, collecting and forming probes from said fragments; and (c) determining where each of said probes hybridizes to the target nucleic acid according to the method of claim 7, thereby producing a map of the target nucleic acid.

13. A recursive method of sequencing a target nucleic acid comprising the steps of:

(a) mapping said target nucleic acid according to the method of claim 9;

(b) producing a second set of the probes mapped in step (a);

(c) separating, collecting and forming target nucleic acids from said probes;

(d) repeating steps (a) through (c) until the probes produced in step (a) are of a size that can be completely sequenced in one sequencing reaction; and (e) sequencing the probes.

14. A recursive method of sequencing a target nucleic acid comprising the steps of:

(a) mapping said target nucleic acid according to the method of claim 10;

(b) producing a second set of the probes mapped in step (a);

(c) separating, collecting and forming targets from said probes;

(d) repeating steps (a) through (c) until the probes produced in step (a) are of a size that can be completely sequenced in one sequencing reaction; and (e) sequencing the probes.

15. A recursive method of sequencing a target nucleic acid comprising the steps of:

(a) mapping said target nucleic acid according to the method of claim 11;

(b) producing a second set of the probes mapped in step (a);

(c) separating, collecting and forming targets from said probes;

(d) repeating steps (a) through (c) until the probes produced in step (a) are of a size that can be completely sequenced in one sequencing reaction; and (e) sequencing the probes.

16. A recursive method of sequencing a target nucleic acid comprising the steps of: (a) mapping said target nucleic acid according to the method of claim 12; (b) producing a second set of the probes mapped in step (a); (c) separating, collecting and forming targets from said probes; (d) repeating steps (a) through (c) until the probes produced in step (a) are of a size that can be completely sequenced in one sequencing reaction; and (e) sequencing the probes.

* * * * *